(12) United States Patent
Kelm et al.

(10) Patent No.: US 12,119,104 B2
(45) Date of Patent: Oct. 15, 2024

(54) AUTOMATED CLINICAL WORKFLOW

(71) Applicant: Siemens Healthcare GmbH, Erlangen (DE)

(72) Inventors: Michael Kelm, Erlangen (DE); Srikrishna Prasad, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 229 days.

(21) Appl. No.: 16/991,229

(22) Filed: Aug. 12, 2020

(65) Prior Publication Data

US 2021/0065886 A1    Mar. 4, 2021

(30) Foreign Application Priority Data

Aug. 30, 2019   (EP) ..................... 19194504

(51) Int. Cl.
| | |
|---|---|
| G16H 40/20 | (2018.01) |
| G06F 9/455 | (2018.01) |
| G06F 16/583 | (2019.01) |
| G16H 15/00 | (2018.01) |
| G16H 30/20 | (2018.01) |
| G16H 30/40 | (2018.01) |

(Continued)

(52) U.S. Cl.
CPC ......... *G16H 40/20* (2018.01); *G06F 9/45558* (2013.01); *G06F 16/5854* (2019.01); *G16H 15/00* (2018.01); *G16H 30/20* (2018.01); *G16H 30/40* (2018.01); *G16H 50/20* (2018.01); *G16H 50/70* (2018.01); *G06F 2009/45583* (2013.01); *G06F 2009/45595* (2013.01); *H04L 67/10* (2013.01)

(58) Field of Classification Search
CPC ........ G16H 15/00; G16H 40/20; G16H 30/20; G16H 30/40; G16H 50/20; G16H 50/70; G16H 10/60; G06F 9/45558; G06F 16/5854; G06F 2009/45583; G06F 2009/45595; H04L 67/10; G06Q 10/103
USPC ............................................................ 705/3
See application file for complete search history.

(56) References Cited

U.S. PATENT DOCUMENTS

| | | |
|---|---|---|
| 2012/0035963 A1 | 2/2012 | Qian et al. |
| 2012/0130223 A1* | 5/2012 | Reicher ............... G16H 30/40 |
| | | 600/407 |

(Continued)

FOREIGN PATENT DOCUMENTS

| | | | |
|---|---|---|---|
| CN | 102365641 A | 2/2012 | |
| WO | WO-2019224689 A1 * | 11/2019 | ............ H02J 7/0013 |

OTHER PUBLICATIONS

Craddock RC, Tungaraza RL, Milham MP, "Connectomics and new approaches for analyzing human brain functional connectivity", Mar. 25, 2015, Gigascience, 4:13. (Year: 2015).*

(Continued)

*Primary Examiner* — Rachelle L Reichert
*Assistant Examiner* — Amanda R. Covington
(74) *Attorney, Agent, or Firm* — Harness, Dickey & Pierce, P.L.C.

(57) ABSTRACT

Various examples of embodiments of the invention generally relate to automating a clinical workflow, the clinical workflow including an analysis of one or more medical datasets and generation of a medical report based on the analysis. For example, machine-learning algorithms may be used for the analysis. The medical report may be generated based on one or more report templates.

16 Claims, 7 Drawing Sheets

(51) Int. Cl.
 G16H 50/20 (2018.01)
 G16H 50/70 (2018.01)
 H04L 67/10 (2022.01)

(56) References Cited

U.S. PATENT DOCUMENTS

| | | | |
|---|---|---|---|
| 2013/0224694 A1* | 8/2013 | Moore | G09B 19/0092 434/127 |
| 2015/0169652 A1* | 6/2015 | Nuraliev | G06F 16/211 707/805 |
| 2016/0209995 A1* | 7/2016 | Jeon | G06T 5/003 |
| 2017/0323442 A1* | 11/2017 | Suehling | G06N 5/046 |
| 2017/0337329 A1 | 11/2017 | Liu et al. | |
| 2018/0137244 A1* | 5/2018 | Sorenson | G16H 30/20 |
| 2019/0102700 A1* | 4/2019 | Babu | G06N 5/025 |
| 2019/0156947 A1* | 5/2019 | Nakamura | G16H 50/20 |
| 2019/0356137 A1* | 11/2019 | Balarajashetty | H02J 7/00036 |

OTHER PUBLICATIONS

ACR American College of Radiology "Prostate Imaging Reporting & Data System (PI-RADS)" ACR American College of Radiology, PI-RADS v2.1 Module, https://www.acr.org/Clinical-Resources/Reporting-and-Data-Systems/PI-RADS, (aufgerufen am Oct. 9, 2019).
Extended European Search Report for European Application No. 19194504.7 dated Feb. 19, 2020.

\* cited by examiner

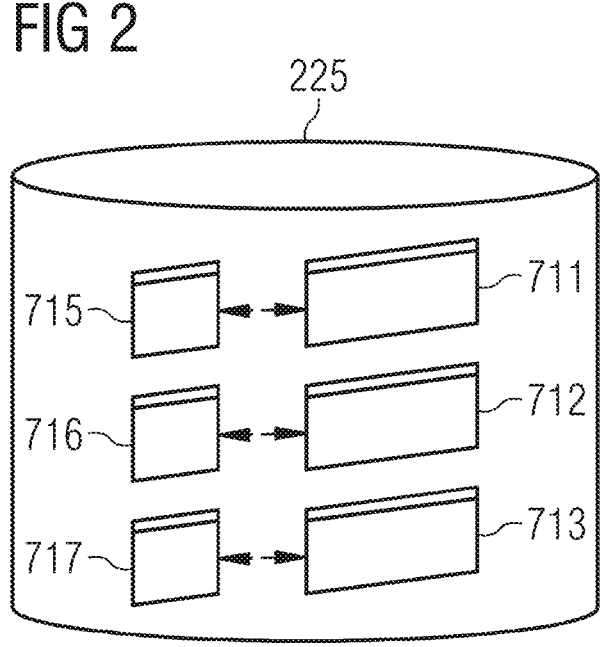
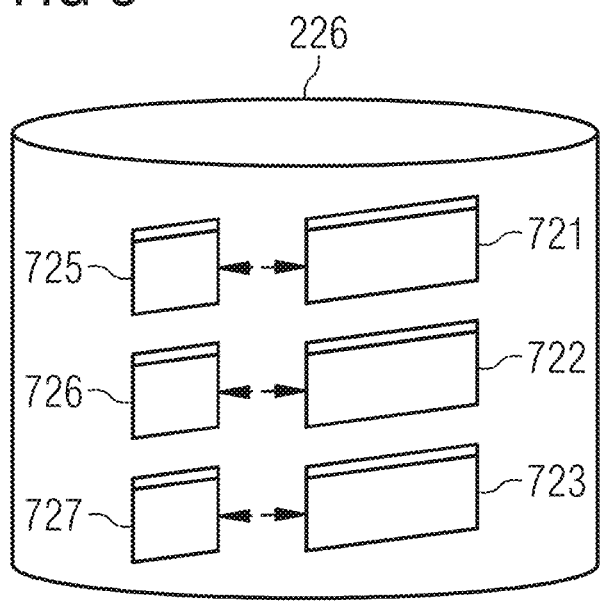

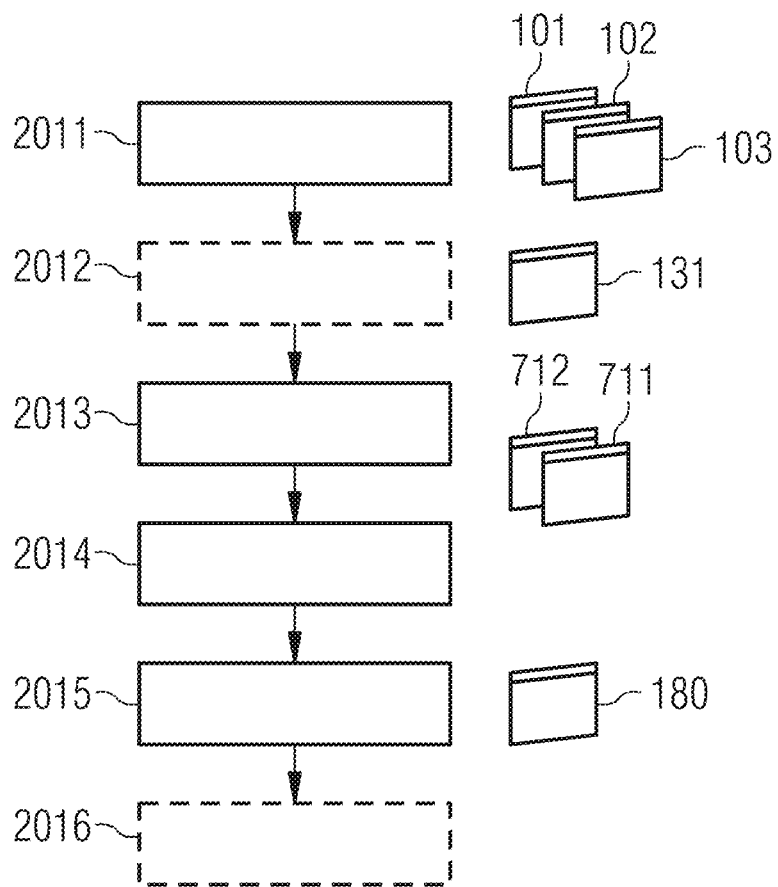
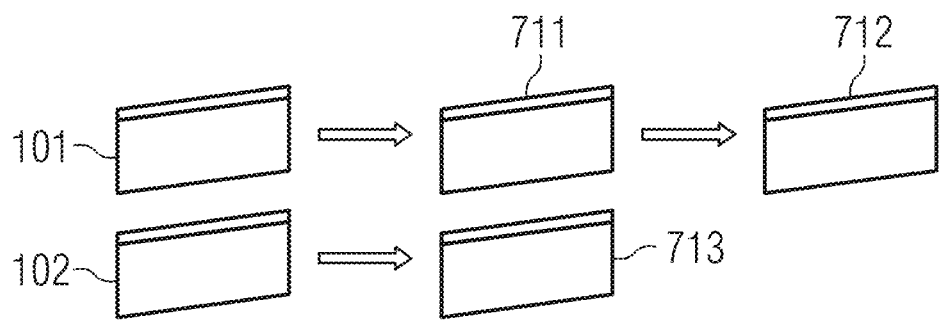

AUTOMATED CLINICAL WORKFLOW

PRIORITY STATEMENT

The present application hereby claims priority under 35 U.S.C. § 119 to European patent application number EP 19194504.7 filed Aug. 30, 2019, the entire contents of which are hereby incorporated herein by reference.

FIELD

Various examples of embodiments of the invention generally relate to automating a clinical workflow, the clinical workflow including an analysis of one or more medical datasets and generation of a medical report based on the analysis.

BACKGROUND

In the clinical workflow, one or more medical imaging datasets are acquired using one or more imaging modalities. Then, the medical imaging datasets are analyzed by a user, e.g., by a radiologist and/or a pathologist, and a medical report is drawn up by the radiologist. The medical report can generally pertain to radiological and/or pathological or other medical-relevant information.

Such techniques face certain restrictions and drawbacks.

For example, evaluating the medical imaging datasets requires significant time. Also, drawing up the medical report requires significant time.

Often, the medical report includes a significant subjective component depending on the particular radiologist drawing up the medical report. For example, the structure and degree of detail included in the medical report can depend on the radiologist. This can sometimes impose challenges on the radiologist in terms of time management and available time for drawing up a complete and well-structured medical report.

SUMMARY

The inventors have discovered that there is a need for techniques that support clinical personnel in the evaluation of medical imaging datasets and the generation of medical reports.

The features of the claims define embodiments.

A computer-implemented method of at least one embodiment includes obtaining one or more medical datasets of a patient. The method also includes triggering a selection of one or more algorithms from an algorithm repository. The algorithm repository includes multiple candidate algorithms. The selection is based on the one or more medical datasets. The method also includes providing the one or more medical datasets as an input to the one or more algorithms. The method also includes triggering execution of the one or more algorithms. The one or more algorithms provide an evaluation of the one or more medical datasets. The method further includes triggering a generation of a medical report based on an output of at least one of the one or more algorithms.

A computer program or a computer program product or a computer-readable storage medium of at least one embodiment includes program code. The program code can be loaded and executed by at least one processor. Upon executing the program code, the at least one processor performs a method of at least one embodiment. The method includes obtaining one or more medical datasets of a patient. The method also includes triggering a selection of one or more algorithms from an algorithm repository. The algorithm repository includes multiple candidate algorithms. The selection is based on the one or more medical datasets. The method also includes providing the one or more medical datasets as an input to the one or more algorithms. The method also includes triggering execution of the one or more algorithms. The one or more algorithms provide an evaluation of the one or more medical datasets. The method further includes triggering a generation of a medical report based on an output of at least one of the one or more algorithms.

A device of at least one embodiment includes a control circuitry configured to load and execute program code. Upon executing the program code the control circuitry is configured to: obtain one or more medical datasets of a patient. The control circuitry is also configured to trigger a selection of one or more algorithms from an algorithm repository. The algorithm repository includes multiple candidate algorithms. The selection is based on the one or more medical datasets. The control circuitry is also configured to provide the one or more medical datasets as an input to the one or more algorithms. The control circuitry is also configured to trigger execution of the one or more algorithms. The one or more algorithms provide an evaluation of the one or more medical datasets. The control circuitry is further configured to trigger a generation of a medical report based on an output of at least one of the one or more algorithms.

At least one embodiment is directed to a computer-implemented method, comprising:
  obtaining one or more medical datasets of a patient;
  triggering a selection of one or more algorithms from an algorithm repository including multiple candidate algorithms, the selection being based on the one or more medical datasets obtained;
  providing the one or more medical datasets as an input to the one or more algorithms and triggering execution of the one or more algorithms, the one or more algorithms providing an evaluation of the one or more medical datasets; and
  triggering a generation of a medical report based on an output of at least one of the one or more algorithms.

BRIEF DESCRIPTION OF THE DRAWINGS

FIG. 2 schematically illustrates a repository for evaluation algorithms that can evaluate medical datasets according to various examples.

FIG. 3 schematically illustrates a repository for medical report templates that can be used to generate medical reports according to various examples.

FIG. 6 is a flowchart of a method according to various examples.

FIG. 7 schematically illustrates multiple evaluation algorithms used for evaluation a medical dataset according to various examples.

DETAILED DESCRIPTION OF THE EXAMPLE EMBODIMENTS

Figure 1:
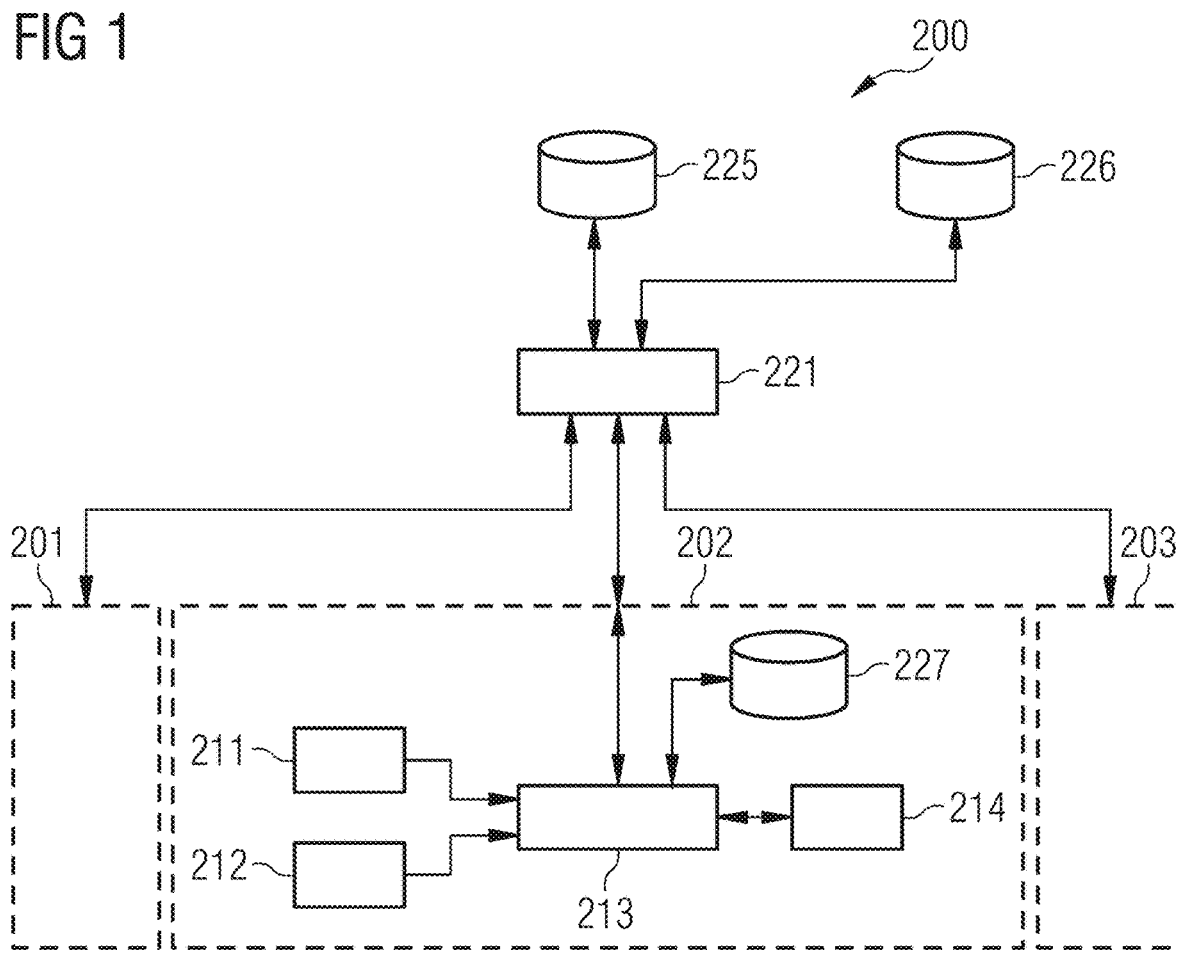
FIG. 1 schematically illustrates a system for automizing a clinical workflow according to various examples.

The above and other elements, features, steps, and concepts of the present disclosure will be more apparent from the following detailed description in accordance with example embodiments of the invention, which will be explained with reference to the accompanying drawings.

Some examples of the present disclosure generally provide for a plurality of circuits, data storages, connections, or electrical devices such as e.g. processors. All references to these entities, or other electrical devices, or the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that their function and general purpose become apparent to a person skilled in the art. Any connection, or communication, or coupling between functional blocks, devices, components, or other physical or functional units shown in the drawings or described herein may also be implemented by an indirect connection or coupling. A communication between devices may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A computer-implemented method of at least one embodiment includes obtaining one or more medical datasets of a patient. The method also includes triggering a selection of one or more algorithms from an algorithm repository. The algorithm repository includes multiple candidate algorithms. The selection is based on the one or more medical datasets. The method also includes providing the one or more medical datasets as an input to the one or more algorithms. The method also includes triggering execution of the one or more algorithms. The one or more algorithms provide an evaluation of the one or more medical datasets. The method further includes triggering a generation of a medical report based on an output of at least one of the one or more algorithms.

As used herein, triggering may generally refer to performing the execution locally or transmitting a command to offload the execution to another entity.

A computer program or a computer program product or a computer-readable storage medium of at least one embodiment includes program code. The program code can be loaded and executed by at least one processor. Upon executing the program code, the at least one processor performs a method of at least one embodiment. The method includes obtaining one or more medical datasets of a patient. The method also includes triggering a selection of one or more algorithms from an algorithm repository. The algorithm repository includes multiple candidate algorithms. The selection is based on the one or more medical datasets. The method also includes providing the one or more medical datasets as an input to the one or more algorithms. The method also includes triggering execution of the one or more algorithms. The one or more algorithms provide an evaluation of the one or more medical datasets. The method further includes triggering a generation of a medical report based on an output of at least one of the one or more algorithms.

Such program code can be used to execute the method described above. Further, throughout this text various examples will be described in the context of a method and the program code can be configured to provide corresponding logic.

A device of at least one embodiment includes a control circuitry configured to load and execute program code. Upon executing the program code the control circuitry is configured to: obtain one or more medical datasets of a patient. The control circuitry is also configured to trigger a selection of one or more algorithms from an algorithm repository. The algorithm repository includes multiple candidate algorithms. The selection is based on the one or more medical datasets. The control circuitry is also configured to provide the one or more medical datasets as an input to the one or more algorithms. The control circuitry is also configured to trigger execution of the one or more algorithms. The one or more algorithms provide an evaluation of the one or more medical datasets. The control circuitry is further configured to trigger a generation of a medical report based on an output of at least one of the one or more algorithms.

For example, the device could be implemented by a computer or a medical imaging device, or a medical analysis device, or a server.

Such device may execute the method described above. Further, throughout this text various examples will be described in the context of a method and the control circuitry of the device can be configured to execute corresponding logic.

It is to be understood that the features mentioned above and those yet to be explained below may be used not only in the respective combinations indicated, but also in other combinations or in isolation without departing from the scope of the invention.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Hereinafter, techniques will be described that can find application along a clinical workflow. In the examples described herein, the clinical workflow can be associated with one or more of the following items: (i) evaluation of one or more medical datasets; (ii) generation of medical reports; and (iii) visualization of results of the evaluation.

The techniques described herein can assist clinical personnel, such as radiologists, in tasks related to these items of the clinical workflow. This can be achieved by automation. The techniques described herein can employ computer-implemented logic. The computer-implemented logic can continuously interact with the clinical personnel along the clinical workflow to provide for a smaller or larger degree of automation, depending on the implementation.

The techniques described can be used to implement a medical analytics platform. The medical analytics platform can provide access to evaluation algorithms that can perform a qualitative and/or quantitative analysis on medical datasets. The medical analytics platform can help to generate a medical report, e.g., by pre-filling certain sections thereof and/or generation of the entire medical report in an automated manner. Alternatively or additionally to such generation of the medical report, it would be possible to provide a visualization of outputs of one or more selected evaluation algorithms.

As a general rule, the medical datasets as described herein can include medical imaging datasets and non-imaging medical datasets: in other words, the medical datasets could be implemented by medical images or medical measurements such as blood values, genetic information, etc. As a general rule, the techniques described herein are not limited to one or more specific types of medical imaging datasets or, in particular, are not limited to one or more specific imaging modalities. Examples of imaging modalities that can interact with the techniques described herein include, but are not limited to: X-ray imaging; computer tomography (CT); ultrasound imaging; positron emission tomography (PET); and magnetic resonance imaging (MRI). Non-imaging medical datasets can also widely vary, depending on the scenario. Examples of non-imaging medical datasets include: blood tests; electrocardiograms; samples such as stool samples or urine samples; etc.

The techniques described herein cover various items of the clinical workflow.

A first aspect of the techniques described herein generally relates to the selection of one or more evaluation algorithms from an algorithm repository. The evaluation algorithms can be used to evaluate medical datasets. The evaluation can be automated to a larger or smaller degree. According to some examples, one or more selection algorithms are used to implement the selection. According to some examples, a user-interaction mode for the selection of the one or more evaluation algorithms may be selected. According to some examples, the selection of the one or more evaluation algorithms takes into consideration the medical report that is to be generated based on outputs of the one or more evaluation algorithms.

By such techniques, a tailored and accurate selection of the one or more evaluation algorithms is possible. Such techniques are based on the finding that sometimes it can be difficult to determine which evaluation algorithm is appropriate for the analysis of a certain medical dataset. Typical questions when selecting the one or more evaluation algorithms are: Which evaluation algorithm to choose for a certain body part? Which algorithm to choose for a certain imaging modality? Which algorithm to choose for a certain disease? Techniques described herein help to facilitate the proper selection of one or more evaluation algorithms using various strategies.

A second aspect of the techniques described herein generally relates to the distribution of computer-implemented logic, e.g., between on-premise servers and off-premise servers. For example, certain computer-implemented logic may be implemented on a local server in a hospital local network. Other computer-implemented logic may be implemented off-premise on a server outside of the hospital local network that may be reached via the Internet. According to the techniques described herein, an interaction between such different servers can be implemented. At least some of the computer-implemented logic associated with the clinical workflow described herein can be implemented by a cloud-computing service. In particular, strategies for instantiation or pre-instantiation of compute containers for the cloud-computing server are described. The strategies include an allocation of such containers to certain computational tasks associated with different steps along the clinical workflow, e.g., the selection of the one or more evaluation algorithms, the execution of the one or more evaluation algorithms, the selection of a medical report template, the generation of the medical report, and so on. By such techniques, it becomes possible to efficiently implement the computer-implemented logic. Computational resources can be reduced. Data traffic may be reduced. Computational latency may be reduced.

A third aspect of the techniques described herein generally relates to the interaction between the automated components of the clinical workflow and the user along the clinical workflow. According to the techniques described herein, continued bi-directional user interfacing is possible that provides continued guidance to the user along the clinical workflow and helps to streamline the user interaction, minimizing dead times and possibilities for human error.

In the various techniques described herein, features pertaining to one of these aspects can be combined with features pertaining to another one of these aspects. Sometimes, features pertaining to one of these aspects will be described together with features pertaining to another one of these aspects; but it should be understood that it is possible to isolate such features from each other and implement independently from each other.

According to the techniques described herein, a degree of automation of the clinical workflow can vary. For example, according to some techniques, it would be possible that the evaluation of the medical datasets is implemented using one or more evaluation algorithms. Then, an output of the one or more evaluation algorithms can be presented to clinical personnel and the clinical personnel can subsequently manually draw up the medical report based on the output. Alternatively or additionally, it would also be possible that the medical report is generated in a semi-automated or fully automated manner, e.g., using a report template used to configure the medical report. Still further, alternatively or additionally, it would be possible that the one or more evaluation algorithms used for the evaluation of the medical datasets are selected in a semi-automated or fully automated manner. Here, it would be possible that one or more selection algorithms are used to assist clinical personnel in the selection. The techniques described herein facilitate user interaction along the various items of the clinical workflow. For instance, a user may desire to manually annotate an output of an evaluation algorithm. This may be possible by appropriate user interaction. Then, upon receiving such user feedback on the output of the evaluation algorithm, it would be possible that the evaluation algorithm and/or one or more further evaluation algorithms are re-executed, taking the user feedback as a prior. Similarly, a user may adjust the content of a medical report that is automatically generated based on a medical report template. This adjustment of the medical report may trigger certain adjustments upstream of the clinical workflow; e.g., the result of another evaluation report may be selected, etc. A user may also choose or select the preferred user-interaction mode. Thereby, the acquisition of user input may be facilitated.

In the various techniques described herein, cloud-based computing may or may not be employed, in addition to local computing. For example, some or all of the computer-implemented logic described herein may be executed by a local server. A local server can denote a server that is located in a local-area network operated by the operator of the clinical environment with which the clinical personnel, medical equipment etc. described herein is associated. For example, the local server may be located on the premise of the clinic. The local server may also be located in a server farm and operated by a third-party operate on behalf of the operator of the clinic. The local server may be different from a cloud-computing server. Here, a cloud-computing operator may operate a server farm including multiple cloud-computing servers and may distribute computational resources between different users. This can be done by relying on virtual machines and/or containers. The cloud-computing server may not fixedly associate hardware with a respective user. The operator of the clinic may not have access to or be in charge of the hardware associated with the cloud-computing servers.

FIG. 1 schematically illustrates a system 200 according to various examples. The system 200 can be used for assisting clinical personnel in the evaluation of medical datasets and in the generation of medical reports. The system 200 can implement a medical analytics platform.

The system 200, in the example of FIG. 1, includes three local networks 201-203. Each local network 201-203 is associated with a respective operator. Each local network 201-203 can be associated with a hospital or a set of hospitals. Different ones of the local networks 201-203 may have different operators. Accordingly, a user of, e.g., the local network 202 may not have access to the local network 201 or the local network 203. In FIG. 1, details are only illustrated in connection with the local network 202; however, generally, it would be possible that the local networks 201, 203 are configured in the same manner as the local network 202.

The local network 202 includes medical devices 211-212. For example, the medical devices 211-212 may include one or more medical imaging devices, e.g., an x-ray imaging device, a computer tomography scanning device, a magnetic resonance imaging device. The medical devices 211-212 may also include one or more medical laboratory devices that can determine one or more clinical diagnostics of a patient. Examples include blood gas, cardiac, coagulation, diabetes, urin analysis, or other clinical measurements.

The medical devices 211-212 can provide medical datasets as an output. Based on these medical datasets, conventionally, the physician can draw up a medical report based on a diagnose. The diagnose is obtained by evaluating the medical datasets. According to the techniques described herein, the system 200 can assist the physician in these tasks.

For this purpose, the local network 202 also includes a server 213 that is connected to the medical devices 211-212. For example, the server 213 can receive the medical datasets provided as an output by the medical devices 211-212.

The local network 202 also includes a human-machine interface (HMI) 214. Input data can be received from a user via the HMI 214. Output data can be provided to the user via the HMI 214. Thereby, continued user guidance and assistance along the clinical workflow is possible.

The local networks 201-203 are in communication with a central server 221, e.g., via the Internet (the central sever 221 could be labeled off-premise server, in contrast to the on-premise server 213). For example, the server 221 can be operated and maintained by an operator different from the operators of the local networks 201-203. For instance, a server 221 can provide cloud-computing services. Computational resources available at the server 221 can be distributed among computing tasks associated with each one of the local networks 201-203.

As illustrated in FIG. 1, various databases 225-227 are provided; the databases 225-227 can implement repositories for data. For instance, the database 225 as well as the database 226 is associated with the server 221; while the database 227 is associated with the server 213. These associations are an example only. In other examples, it would be possible that also the database 227 is associated with the server 221. It would also be possible that the databases 225-226 are associated with the server 213.

The system 200 as illustrated in FIG. 1 is characterized by the coexistence of the local networks 201-203 and the central server 221. As a general rule, the central server 221 is optional. In some examples, the computer-implemented logic that is implemented by the server 221 may be implemented on the server 213. For instance, such examples, the databases 225-226 can be directly coupled to the server 213.

Next, details with respect to the databases 225-227 are described in connection with the following FIGS.

FIG. 2 schematically illustrates aspects with respect to the database 225. The database 225 is configured to implement a repository for evaluation algorithms 711-713.

As a general rule, the evaluation algorithms 711-713 can be applied to one or more medical datasets to analyze the one or more medical datasets. Such analysis can correspond to performing a medical diagnosis. For example, the analysis can extract one or more medical conditions of the patient from the one or more medical datasets. For example, the analysis can determine one or more abnormal or pathological medical conditions from the one or more medical datasets. For example, the analysis can quantify one or more medical conditions based on the one or more medical datasets.

At least some of the evaluation algorithms 711-730 can employ techniques of machine learning, sometimes also labeled artificial intelligence (AI). For instance, some of the evaluation algorithms 711-713 could implement an artificial neuronal network such as a convolutional neural network for feature detection/feature classification. For example, segmentation of certain anatomical parts of the patient could be implemented using such artificial neuronal networks. Other machine learning techniques are conceivable, e.g., Support Vector Machines, etc.

As a general rule, it would be possible that the database 225 can be populated by multiple users. For example, the server 221 may provide access to the evaluation algorithm repository to enable third parties to upload new evaluation algorithms In particular, the database 225 may be populated not only by the users employing the evaluation algorithms 711-713; but also by other users. For example, such other users may be specialized in the generation of evaluation algorithms 711-713. As such, the database 225 can implement a platform bringing together users generating the evaluation algorithms 711-713, and users applying the evaluation algorithms 711-713.

The database 225 can store a wide variety of evaluation algorithms 711-713. In particular, different ones of the evaluation algorithms 711-713 may accept different kinds and types of inputs. In other words, different ones of the evaluation algorithms 711-713 may operate based on different medical datasets. For example, a first one of the evaluation algorithms 711-713 may expect a spine MRT medical imaging dataset as an input; while a second one of the evaluation algorithms 711-713 may expect a brain CT medical imaging dataset as the input. Thus, as will be appreciated, the evaluation algorithms 711-713 may differ with respect to the required input. Alternatively or additionally, it would also be possible that the evaluation algorithms 711-713 differ with respect to the kind of evaluation and, thus, the type of output. For example, while two of the evaluation algorithms 711-713 may both operate based on liver MRT medical imaging datasets, one of those evaluation algorithms may evaluate the liver size, while the other one of those evaluation algorithms may evaluate a fat content of the liver.

As a general rule, the particular evaluation algorithms 711-713 included in the database 225 are not germane for the functioning of the techniques described herein. In particular, the techniques described herein can flexibly accommodate various different kinds and types of evaluation algorithms 711-713, and, hence, provide a framework for the application of such evaluation algorithms 711-713. The concrete implementation of each individual evaluation algorithms 711-713 on the other hand is out of scope of the techniques described herein.

To facilitate a selection of one or more appropriate evaluation algorithms 711-713, the database 225 also stores meta data 715-717. This is generally optional. The meta data 715-717 may be provided for each one of the evaluation algorithms 711-713. The meta data 715-717 describes properties of the respective evaluation algorithm 711-713. For example, the meta data 715-717 can describe a required input of the respective evaluation algorithm 711-713. For example, the meta data 715-717 can describe a respective output of the respective evaluation algorithm 711-713. More specifically, it would be possible that the meta data is indicative of a physiological-diagnostic content description of the input and the output of the evaluation algorithms 711-713. The meta data 715-717 may thus provide a semantic description of the evaluation algorithms 711-713. The meta data 715-717 facilitates selection of the appropriate evaluation algorithm 711-713 for a given clinical task. The meta data 715-717 can be used by suppliers of the evaluation algorithms 711-713 to appropriately annotate the functional characteristics of the provided evaluation Using the evaluation algorithm 711-713, a part of the clinical workflow can be automated. This is because the evaluation of the medical dataset can be fully or partly automated.

In the various examples described herein, automating this part of the clinical workflow associated with the diagnosis of the medical condition can be complemented by an automation of the generation of the medical report. For this, the generation of the medical report can be configured in accordance with a report template. The report template can be retrieved from the database 226. Details with respect to the database 226 are illustrated in connection with FIG. 3.

FIG. 3 schematically illustrates aspects with respect to the database 226. The database 226 is configured to implement a repository for medical report templates 721-723. The medical report templates 721-723 can be applied to configure the generation of a medical report. More specifically, it would be possible that the generation of the medical report is partly automated using the medical report templates 721-723. In particular, based on the medical report template 721-723 the medical report can be generated in a semi-automated or fully automated manner.

To give an example, it would be possible that the medical report templates 721-723 specify a structure of the medical report; this structure can be used when generating the medical report. For example, it would be possible that the medical report templates 721-723 specify a content of the medical report such that the generation of the medical report can be automated. For example, the content of the medical report can specify the reported medical conditions.

Again, as already explained in connection with the database 225, it would be possible that the database 226 can be populated by multiple users. In particular, the database 226 may be populated not only by the users employing the report templates 721-723; but also by other users. For example, such other users may be specialized in the generation of medical report template 721-723. As such, the database 226 can implement a platform bringing together users generating the medical report templates 721-723, and users applying the medical report templates 721-723 for the generation of medical reports.

The database 226 can store a wide variety of medical report templates 721-723. In particular, different ones of the medical report template 721-723 may configure the generation of the medical report to rely on different kinds and types of inputs. In other words, different ones of the medical report templates 721-723 may operate based on the output of different evaluation algorithms 711-713. For example, a first one of the medical report templates may configure the medical report such as to specify a medical condition associated with a brain tumor; while a second one of the medical report templates may configure the medical report such as to specify a medical condition associated with fatty liver disease.

To facilitate a selection of one or more appropriate medical report templates 721-723, the database 226—in the example of FIG. 3—also stores meta data 725-727. This is generally optional. The meta data 725-727 is provided for each one of the medical report templates 721-723. The meta data 725-727 describes properties of the respective medical report template 721-723. For example, the meta data 725-727 can describe a required input of the generation of the associated medical report. For example, the meta data 725-727 can describe a content of the associated medical report that is generated by the respective medical report template 721-723.

As will be appreciated, the number and variety of the conceivable clinical tasks or implementation variants for the clinical workflow is defined by the count of evaluation algorithms 711-713 in the database 225, as well as by the count of medical report template 721-723 and the database 226. Typically, each one of the databases 225-226 will include a large number of entries, e.g., more than 50 entries or even more than 100 entries or even more than 1000 entries, respectively. Thus, a wide variety of possible implementations of the clinical workflow exists. Various techniques are based on the finding that it can be challenging to select the appropriate evaluation algorithm 711-713 from the database 225 for the evaluation of a given medical dataset. Likewise, various techniques are based on the finding that it can be challenging to select the appropriate medical report template 721-723 from the database 226 for configuring the generation of the medical report. Accordingly, in the various examples described herein, it would be possible to employ one or more selection algorithms to facilitate such selection, e.g., of the appropriate evaluation algorithm 711-713 and/or of the appropriate medical report template 721-723. The one or more selection algorithms can be stored in a database 227. Details with respect to the database 227 are explained next in connection with FIG. 4.

Figure 4:
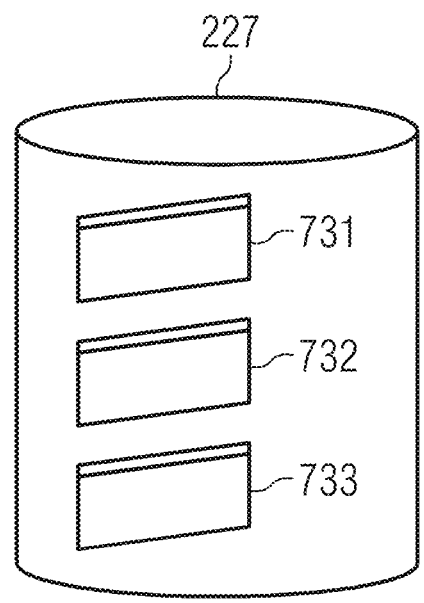
FIG. 4 schematically illustrates a repository for selection algorithms that can select one or more evaluation algorithms for evaluating a medical dataset according to various examples.

FIG. 4 schematically illustrates aspects with respect to the database 227. The database 227 is configured to implement a repository for selection algorithms 731-733. The selection algorithms 731-733 can be applied to select one or more evaluation algorithm 711-713 from the database 225 (cf. FIG. 2) and/or to select one or more medical report templates 721-723 from the database 226). In part particular, based on the selection algorithm 731-733, the selection of the one or more evaluation algorithm 711-713 can be implemented in a semi-automated or fully-automated manner.

As will be appreciated from the discussion of FIG. 1 to FIG. 4 above, the clinical workflow of the evaluation of one or more medical datasets and the generation of an associated medical report can rely on computer-implemented logic in various manners; examples have been described in connection with the evaluation of the one or more medical datasets using evaluation algorithms (cf. FIG. 2), the generation of the medical report and the configuring of the generation medical report based on one or more medical report templates (cf. FIG. 3), as well as the selection of the one or more evaluation algorithms using one or more selection algorithms (cf. FIG. 4).

As a general rule, it would be possible that such and other computer-implemented logic is implemented by a cloud-computing service. Aspects with respect to the cloud-computing service are illustrated in connection with FIG. 5.

Figure 5:
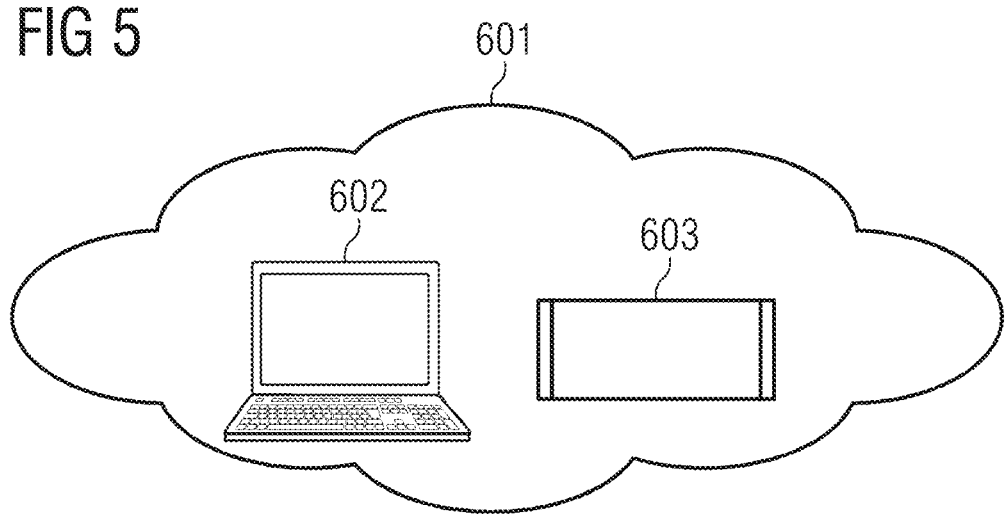
FIG. 5 schematically illustrates a cloud-computing service according to various examples.

FIG. 5 schematically illustrates aspects with respect to a cloud-computing service 601. The cloud-computing service 601 can be used to implement computer-implemented logic in a cloud-computing center such as a server farm. The cloud-computing center may define a hardware layer and a functional layer. The hardware layer may be transparent to users of the cloud-computing service 601. For example, a user requesting execution of one or more of the evaluation algorithm 711-713 may not be aware of the underlying hardware used by the cloud-computing service 601 to execute the evaluation algorithm 711-713.

With respect to FIG. 1: for instance, the server 221 may implement a hardware layer of the cloud-computing service 601. The cloud-computing service 601 may offer various options for assigning computational resources of the hardware layer to a particular task. To such options are illustrated in FIG. 5. A first option relies on a virtual machine 602. A second option relies on a container 603.

Each virtual machine 602 may run a unique operating system. Virtual machines with or without different operating systems can run on the same physical server 221. Examples of operating systems include: Windows; Unix; Linux. Each virtual machine 602 typically has its own binaries, libraries, and applications that it services. A typical storage requirement of a virtual machine is in the order of gigabytes. Typically, the instantiation of a virtual machine may require minutes. Once instantiated, the virtual machine may pre-provision a certain predefined amount of computational resources for computational tasks that are to be assigned to the respective virtual machine 602 in the future.

Differently, multiple containers 603 may share the same operating system. In particular, a container engine may be implemented by the operating system and the container engine may support multiple containers. Instantiation of the containers 603 can include loading the container engine and executing the container engine using the operating system. The container engine can support instantiation of multiple containers. Thus, multiple containers share the same instantiation of the operating system. Such shared components may typically not be altered by the containers. Thus, computational tasks implemented by the containers may use libraries, binaries, and applications provided by the operating system to multiple containers in read-only, wherein the multiple containers are executed contemporaneously. This increases a failure redundancy and robustness. Containers can be quickly instantiated; typically, the instantiation of a container can be much faster than the instantiation of a virtual machine. For example, the instantiation of a container may require seconds.

For example, so-called singularity-type containers 603 may be used. Such singularity-type containers can be used to package entire workflows, software, libraries, and data. Another option relies on so-called Docker-type containers 603.

FIG. 6 is a flowchart of a method according to various examples. In FIG. 6, optional boxes are illustrated using dashed lines.

The method of FIG. 6 is computer implemented. For example, the method of FIG. 6 can be implemented by a device that includes control circuitry. The device may be implemented by a server, e.g., the server 213 of the local network 202 (cf. FIG. 1). For example, the method of FIG. 6 can be implemented by a processor of a device upon loading program code from a memory of the device and executing the program code. For example, the program code may be provided by a computer program or a computer-program product or a computer-readable storage medium. Hereinafter, an exemplary scenario is described in which the device is embodied by a server; but other scenarios are conceivable.

FIG. 6 illustrates aspects of a clinical workflow, the clinical workflow including (i) obtaining medical datasets; (ii) evaluating the medical datasets; and (iii) generating a medical report based on the evaluating. The method of FIG. 6 helps to automate partially or fully the clinical workflow for the evaluation of one or more medical datasets and the associated generation of the medical report.

At box 2011, the one or more medical datasets 101-103 are obtained. For instance, the one or more medical datasets 101-103 could be received from one or more medical devices, e.g., medical laboratory devices, medical imaging devices, etc. The one or more medical datasets 101-103 could be pre-generated or could be obtained upon acquisition. Box 2011 may include controlling one or more medical imaging devices to acquire the medical datasets.

The one or more medical datasets 101-103 are associated with the patient. As such, the one or more medical datasets 101-103 include information indicative of one or more medical conditions of the patient.

At optional box 2012, a patient dataset 131 is obtained. The patient dataset 131 includes patient-specific information of the patient. For example, the patient dataset 113 could specify one or more of the following patient-specific information elements: a previous diagnosis of the patient; a therapeutic history of the patient including, e.g., medication, etc.;

Next, at box 2013, the selection of one or more evaluation algorithms is triggered. This can be based on the one or more medical datasets 101-103 obtained at box 2011 and/or based on the patient dataset 131 obtained at box 2012.

Triggering the selection can include: performing the selection locally, e.g., at the server also executing boxes 2011-2012; or transmitting a command to perform the selection, e.g., to a remote server or a cloud computing service (cf. FIG. 5); or providing a user interface via an HMI to enable manual or semi-automatic selection of the one or more evaluation algorithms, e.g., in accordance with a user-interaction mode.

There are various options available for implementing the selection of the one or more evaluation algorithms. For instance, a manual selection can be facilitated via the HMI. The selection could also be automated partly or fully. In such an automated implementation, it would be possible to rely on one or more selection algorithms (cf. FIG. 4: selection algorithms 731-733). Thus, it would be possible that box 2013 includes providing the one or more medical datasets 101-103 as an input to the one or more selection algorithms and triggering execution of the one or more selection algorithms. Then, the one or more evaluation algorithms 711-712 can be selected based on an output of the one or more selection algorithms.

Again, there are various options available for implementing the selection algorithms. For instance it would be possible that the selection algorithms include AI techniques. Here, it would be possible that, e.g., depending on certain process parameters of the particular clinical workflow—e.g., source of the medical dataset, user, patient, time of the day, etc.—the appropriate evaluation algorithm(s) is(are) selected. Such techniques can rely on recurrent training during use. More specifically, it would be possible that a user input is received and that the selection algorithms are trained based on the user input. Another example could employ a landmark detection to detect physiological features—e.g., certain body regions—in medical imaging datasets. Yet another technique can rely on matching semantic content descriptions of the medical datasets with the meta data 715-717 associated with the evaluation algorithms. More specifically, it would be possible that the selection algorithms are configured to perform a comparison between the meta data 715-717 associated with the candidate evaluation algorithms 711-713 and the physiological features obtained from the landmark detection. Here, it would be possible to employ semantic reasoners. For example, the semantic reasoners may rely on a knowledge graph—e.g., operating based on subject-predicate-object semantic relationships—that structures semantic inter-relationship between different medical properties. For example, physiologic features may be associated with body regions. For example, body regions may be associated with each other. For example, body regions may be associated with diseases. For example, diseases may be associated with imaging modalities that are suitable for diagnosis. For example, evaluation algorithms may be associated with body regions and/or diseases. All such inter-dependencies may be analyzed by the comparison between the meta data 715-717 and medical datasets 101-103.

It has been found that it can be helpful to implement the selection using one or more selection algorithms that are executed by a pre-instantiated container of a cloud-computing service (cf. FIG. 5: container 603). In particular, it has been found that the typical computational resources associated with the execution of such one or more selection algorithms are comparably limited, in particular, if compared to computational resources associated with the execution of one or more evaluation algorithms. Thus, it can be helpful to pre-instantiated a respective container and then assign the computational tasks associated with the execution of the one or more selection algorithms upon demand to that pre-instantiated container—if compared to a scenario in which the container is instantiated upon demand, i.e., when triggering execution of the one or more further algorithms. In particular, such on-demand instantiation can introduce latency and the benefits in terms of computational efficiency can be limited.

Box 2013 provides, as an output, one or more evaluation algorithms selected from a repository of candidate evaluation algorithms (cf. FIG. 2 where the repository is implemented by the database 225).

Then, next, at box 2014, the one or more medical datasets 101-103 are provided as an input to the selected one or more evaluation algorithms 711-712, obtained from box 2013.

Figure 8:
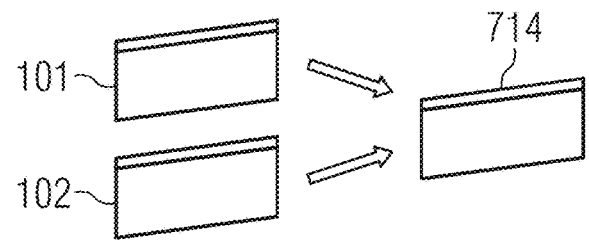
FIG. 8 schematically illustrates multiple evaluation algorithms used for evaluation a medical dataset according to various examples.

As a general rule, various options are available for implementing a mapping between the one or more medical datasets 101-103 and the one or more evaluation algorithms 711-712 selected in box 2013. In other words: different ones of the medical datasets 101-103 may be provided as an input to different ones of the selected evaluation algorithms 711-712. In particular, such mapping can vary with the different types of medical datasets and/or with the different types of evaluation algorithms. FIG. 7 and FIG. 8 illustrate two respective examples. In FIG. 7, the medical dataset 101 is provided as an input to the evaluation algorithms 711 and the medical dataset 102 is provided as an input to the evaluation algorithm 712. In the example of FIG. 7, furthermore, the evaluation of the medical imaging dataset 101 uses multiple evaluation algorithms 711 and 712, wherein an input of the evaluation algorithm 712 is the output of the evaluation algorithm 711. In FIG. 8, the evaluation algorithm 714 receives, both, the medical datasets 101-102 as an input. The scenarios of FIG. 7 and FIG. 8 can be combined with each other.

For example, the scenario FIG. 8 can implement cross-modality evaluation. For example, an MRT imaging dataset 101 could be combined with an CT imaging dataset 102 for the purposes of the analysis by way of the evaluation algorithm 714. This can provide for a high accuracy. The constraints and/or requirements of the inputs to the various evaluation algorithms 711-714 can be specified by corresponding meta data 715-717 (cf. FIG. 2).

Referring again to FIG. 6, at box 2014, execution of those evaluation algorithms 711-712 is triggered. Again, triggering the execution of the evaluation algorithms 711-712 can include: executing the evaluation algorithms 711-712 locally, e.g., at the server also executing boxes 2011-2012; or transmitting a request to perform the selection, e.g., to a remote server or a cloud-computing service (cf. FIG. 5). For example, one or more dedicated or pre-instantiated containers 603 of the cloud-computing service 601 could be used for executing the evaluation algorithms 711-712 at the cloud-computing service 601. In particular, it would be possible that a respective dedicated container 603 of the cloud-computing service 601 is instantiated for each evaluation algorithm 711-712, upon its selection.

It has been found that it can be helpful to implement the execution of the one or more evaluation algorithms using on-demand instantiation of containers, i.e., upon selection of the respective one or more evaluation algorithms and triggering its execution. This is because typically the required computational resources are significant in absolute terms for the execution of evaluation algorithms. For example, the amount of payload data to be handled—i.e., the size of the medical datasets 101-103—can be significant. Furthermore, also the amount of computational resources can significantly vary from evaluation algorithm 711-713 to evaluation algorithm 711-713. I.e., different evaluation algorithms 711-713 can require a significant different amount of computational resources. Still further, sometimes also the runtime environment required by the execution of a particular evaluation algorithm 711-713 can be specific for this particular evaluation algorithm 711-713. For all such reasons, on-demand instantiation of the container 603 and the cloud-computing service 601 upon selection of the respective one or more evaluation algorithms 711-712 can be desirable.

Next, at box 2015, the generation of a medical report 180 is triggered. This is based on an output of the one or more evaluation algorithms 711-712.

As a general rule, it is not required that the medical report 180 is generated/drawn up based on the outputs of all selected one or more evaluation algorithm 711-712 for which execution has been triggered in box 2014. More specifically, at box 2015, the generation of a medical report is triggered based on an output of at least one of the selected one or more evaluation algorithm 711-712.

The generation of the medical report 180 at box 2015 can be automated. For this, the generation of the medical report 180 may be configured based on a medical report template selected and retrieved from a corresponding repository (cf. FIG. 3 where the repository of medical report templates 721-723 is implemented by the database 226). In other words, the medical report can be generated based on the medical report template.

As a general rule, the appropriate medical report template 721-723 may be selected from the database 226 manually by the user. Alternatively or additionally, it would also be possible to assist the user in the selection of the appropriate medical report template 721-723 using one or more report template selection algorithms. The report template selection algorithms may themselves be stored in a respective repository (not illustrated in the FIGS.). Again, it would be possible that the execution of the one or more report template selection algorithms is implemented by a cloud-computing service (cf. FIG. 5: cloud-computing service 601).

At optional box 2016, the medical report 180 and/or a result of the evaluation at box 2014 (i.e., the output of the one or more evaluation algorithms 711-712) can be output to the user via a corresponding HMI (cf. FIG. 1: HMI 214).

The computer-implemented method of FIG. 7 can interact with a user. In particular, continued user interaction along the clinical workflow can be used to tailor the evaluation of the one or more medical datasets 101-103 and the generation of the medical report 180. Details with respect to the user interaction are explained next in connection with FIG. 9.

Figure 9:
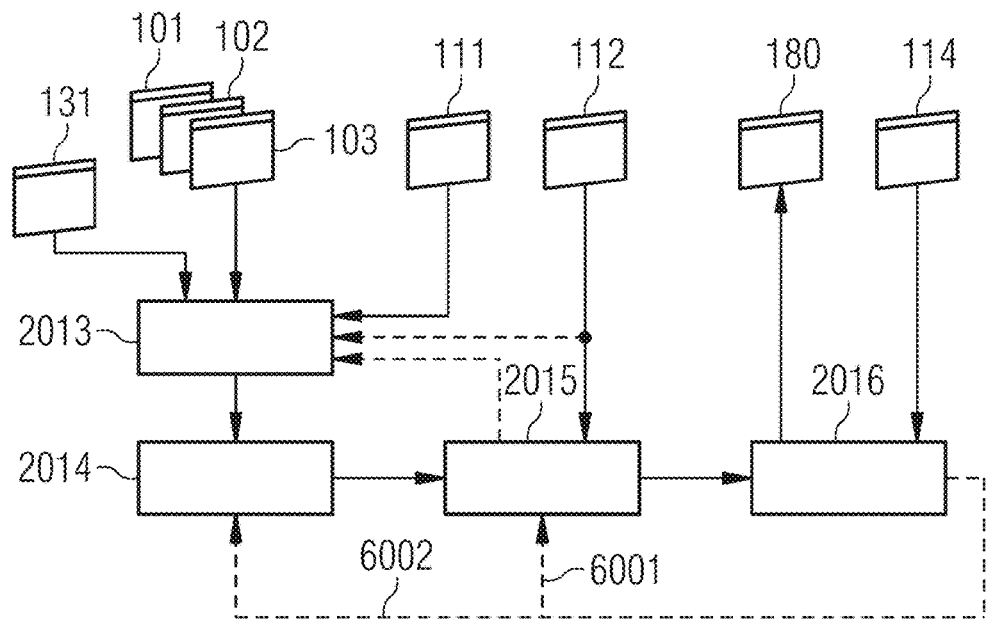
FIG. 9 schematically illustrates user interaction during an automated clinical workflow according to various examples.

FIG. 9 is a functional flowchart of a method according to various examples. The method of FIG. 9 generally corresponds to the method of FIG. 6.

FIG. 9 illustrates aspects with respect to user interaction along the clinical workflow.

First, as illustrated in FIG. 9, the selection of one or more evaluation algorithm 711-712 at box 2013 depends on the medical datasets 101-103, optionally the patient dataset 113 and, further optionally, the user input 111. The user input 111 is received via an HMI, e.g., the HMI 214 (cf. FIG. 1).

In a simple example, it would also be possible that the selection of the one or more evaluation algorithms 711-712 is based on a user-preference setting that is indicated by the user input 111. Accordingly, a given user may specify certain preferred evaluation algorithms 711-713 in the database 225. Alternatively or additionally, it would also be possible that a given user specifies a preferred user-interaction mode for the selection of the one or more evaluation algorithms.

As a general rule, various user-interaction modes may be available. For instance, the user-interaction modes may offer different implementations of the selection of the one or more evaluation algorithms at box 2013 based on the user input 111. For example, different user-interaction modes may vary with respect to the degree of automation of the selection process for example, a first user-interaction mode may be fully automated; here, the user input 111 may not be required. A second user-interaction mode may be fully manual; here, based on an appropriate user interface provided to the user via the HMI, the user may select the one or more evaluation algorithms 711-712 manually. For instance, the user may be presented with the medical datasets 101-103. For instance, in case the medical datasets 101-103 include medical imaging datasets, those may be displayed and a corresponding viewing application may be launched. It would be possible that the patient dataset 131 is output to the user. Then, the user may have all information available to select the one or more evaluation algorithms 711-712 manually. A third user-interaction mode may be partially automated. Here, it would be possible that—e.g., using the one or more selection algorithms 731-733—a pre-selection of one or more evaluation algorithms from the corresponding repository is performed. This pre-selection can then be presented to the user and the user can manually select the one or more evaluation algorithm 711-712 from the pre-selected candidates. For example, it would be possible that the one or more selection algorithms 731-733 provide a ranking of the pre-selected candidates such that such pre-selected candidate evaluation algorithms that are more likely to be finally selected by the user are presented more prominently to the user via the user interface. For example, a sorted list could be presented, wherein the position within the sorted list depends on the rank. Such a scenario is illustrated in Table 1.

TABLE 1

Sorted list for evaluation algorithm selection, in accordance with ranking

| Rank | Evaluation algorithm | Description |
|------|----------------------|-------------|
| 1 | CT Brain A | <<Helpful description for physician>> |
| 2 | CT Brain B | <<Helpful description for physician>> |

For example, it would be possible that different user-interaction modes vary with respect to criteria used for ranking the evaluation algorithms. For instance, factors that may be used in ranking the evaluation algorithms could include one or more of the following: suitability for handling the medical datasets 101-103; a user-preference setting; required computational resources; estimated runtime; frequency of selection of the particular evaluation algorithm in the past; and/or third-party satisfaction level with the quality of the evaluation algorithm; etc. For example, it would be possible that different user-interaction modes vary with respect to a presentation form of the ranked evaluation algorithms.

For illustration, it would be possible that if the user selects one or more of the evaluation algorithms from the sorted list, e.g., as part of the user input 111, the respective selection algorithm is trained accordingly. Thus, recurrent training would be possible to refine the selection algorithm to provide a more relevant ranking.

Another option for the user-interaction modes pertains to providing different implementations for the configuration of the generation of the medical report. Accordingly, it would be possible that different user-interaction modes provide different user-interaction routines for selecting the appropriate medical report template. For instance, a first user-interaction mode may present the user with the choice of a first standard medical report template and a second customized report template. A second user-interaction mode may provide other choices, or the same choice with another ranking.

Various techniques are based on the finding that different users may have different preferences regarding the user-interaction mode. Further, various techniques are based on the finding that the accuracy with which the appropriate one or more evaluation algorithms 711-712 can be selected from the database 225 can vary depending on the user-interaction mode. Still further, various techniques are based on the finding that the time required to select the appropriate one or more evaluation algorithms 711-712 from the database 225 can vary depending on the user-interaction mode.

Accordingly, would be possible to select between multiple user-interaction modes for the selection of the one or more evaluation algorithms 711-712.

There are different strategies conceivable for selecting between the user-interaction modes. For instance, a manual selection of the preferred user-interaction mode could be made by the user. It would also be possible that the selection between the multiple user-interaction modes can be based on an accuracy feedback of previous selections of the one or more evaluation algorithms.

For instance, the factors and/or relative weighting of factors used in the ranking (cf. Table 1) could be adjusted depending on the accuracy feedback.

In this regard, the accuracy feedback can specify whether the output of the selected one or more evaluation algorithms 711-712 is satisfactory for the respective clinical task. An indication that the output of the selected one or more evaluation algorithms 711-712 is satisfactory can be that the user—upon reviewing the output of the selected one or more evaluation algorithms 711-712—does not trigger a re-selection of one or more further evaluation algorithms. As such, it would be possible that the accuracy feedback of the previous selections is determined based on a count of re-selections of the one or more evaluation algorithms from the database 225 based on user inputs, e.g., upon reviewing an output of the initially selected one or more evaluation algorithms.

In FIG. 9, it is illustrated that box 2015—i.e., the generation of the medical report 180—can depend on corresponding user input 112. For example, this can include selecting the appropriate report template from the corresponding repository (cf. FIG. 3: database 226). This selection can depend on the user input 112.

An example medical report template 721-723 is shown in TABLE 2:

TABLE 2

Example of a medical report template

INDICATION: (including the date and value of serum PSA level and any prior biopsy type- TRUS, FUSION, IN BORE, date and results), prior therapy (Radiation, Hormones)
TECHNIQUE: (MRI parameters such as sequence, gradient strengths, etc.)
***
COMPARISON: ***
FINDINGS:
Size: L x W x H cm or V cubic cm (with inclusion of PSA density)
Quality
Hemorrhage: ***
Peripheral zone: ***
Transition zone: ***
Lesion (s) in rank order of severity (highest score- to lowest score, then
by size)
1:
Location: use PIRADS SECTOR LABEL and IMAGE SERIES/NUMBER
Size:
T2:
DWI:
DCE:
Prostate margin: (no involvement, indeterminate, or definite extraprostatic extension): ***
Extra-prostatic extension: ***
Neurovascular bundles: Distance from index lesion or any PIRADS 4/5 lesion to NVB's
Seminal vesicles: ***
Lymph nodes
Other pelvic organs: ***
IMPRESSION:
Range from 1 to 5, depending on likelihood of clinically significant cancer
***

As illustrated in FIG. 9, the user input 112 can also be used to select the appropriate one or more evaluation algorithms 711-712 at 2013. It would be possible that the configuration of the generation of the medical report 180 affects the selection of the one or more evaluation algorithms 711-712. Thus, in other words, the selection of the one or more evaluation algorithms 711-712 can be based on the configuration of the generation medical report 180. This is explained in detail next in connection with FIG. 10.

Figure 10:
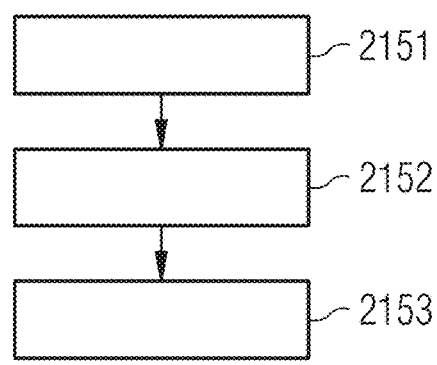
FIG. 10 is a flowchart of a method according to various examples.

FIG. 10 is a flowchart of a method according to various examples. The method of FIG. 10 can be used in connection with boxes 2013 and 2014 (cf. FIG. 6).

FIG. 10 illustrates aspects with respect to the selection of one or more evaluation algorithms 711-714. FIG. 10 illustrates a 2-step selection process.

The techniques of FIG. 10 are based on the finding that, typically, execution of the one or more evaluation algorithms 711-714 requires significant computational resources and, hence, significant time. In order to avoid wait times for the user, the 2-step selection process according to FIG. 10 is employed.

Here, initially, at box 2151 a coarse selection is performed based on the medical datasets 101-103 and optionally based on the patient dataset 131 and/or the user input 111. Then, a first set of evaluation algorithms can be obtained. It would be possible that execution of these evaluation algorithms in the first set can be triggered at box 2152. Then, upon receiving the user input 112 for configuration of the medical report, a fine selection can be implemented, at box 2153. Typically, the output of the evaluation algorithms is already available at box 2153. In particular, a second set of evaluation algorithms can be obtained, wherein the second set is a subset of the first set. In other words, the one or more evaluation algorithms 711-712 can then be selected from the first set, e.g., based on the user input 112 or the configuration of the medical report.

Thus, such scenarios can be associated with a pre-emptive execution of all evaluation algorithms in the first set—even before it is finally decided whether these evaluation algorithms will be included in the second set. For instance, all evaluation algorithms that are likely to be of relevance for the user are pre-emptively executed at box 2152. The output of one or more of these pre-emptively executed evaluation algorithms is then discarded based on the second selection at box 2153. Nonetheless, the user, when configuring the medical report does not have to face wait times to be presented with the output of the finally selected one or more evaluation algorithms 711-714.

Such techniques as explained in connection with FIG. 10 are based on the following findings: While on one hand, medical exams are performed for a reason, usually following the principle of differential diagnosis, the purpose of the exam is not always obvious from the acquired data. For example, a CT scan of the chest could have been indicated due to a (suspected) cardio-vascular disease (CVD) or due to (suspected) lung diseases (e.g. cancer, COPD, ILD) or due to other organs in the chest, such as vertebrae, esophagus or lymph nodes. Even if the reason for requesting the procedure/exam is known, the examining physician may have incidental findings that he/she also needs to report.

On the other hand, evaluation algorithms are typically designed and trained for extracting particular information from a certain kind of medical dataset, e.g., to find nodules in CT lung scans, to quantify calcifications in certain arteries, to trace and anatomically identify vessels in CTA, to segment anatomical structures in T1-weighted brain MR scans, etc. Hence, the challenge arises to select the right one or more evaluation algorithms to apply on the one or more medical datasets resulting from the examination for which medical reporting is to be performed.

A few examples of associated questions are given below:
a) Which best-fit evaluation algorithm(s) to select for certain section (s) of the medical report? For example, procedure, clinical findings, impression etc.
b) Which best-fit evaluation algorithm(s) to select for certain measurement attribute?
c) Which best-fit evaluation algorithm(s) to select for morphological findings of certain body part?
d) Which best-fit evaluation algorithm(s) to select for lesion detection based on location or zonal anatomy?

e) Which best-fit evaluation algorithm(s) to select based on prior indication (e.g. for PIRADs report PSA/Biopsies) or technique (contrast\pulse sequence)?

f) Which best-fit evaluation algorithm(s) to select based on set of findings or based on lesion localization in order to generate natural language based impression?

g) Which best-fit evaluation algorithm(s) to select in order to predict classification or categorization or scoring of disease?

In connection with FIG. 10 techniques have been described above which enable addressing this problem from the perspective of the reporting physician, i.e., under consideration of the question which kind of medical reports the user has to deliver as result of the examination. The required information is then matched with the information extracted by all the evaluation algorithms of the first set. These evaluation algorithms of the first set are executed on the medical datasets. Both, the required information to generate the medical report, as well as the capabilities of each evaluation algorithm of the first set are described with semantic terms using the meta data. Since the evaluation algorithms may run for some time, the execution of the evaluation algorithms of the first set should take place before the user selects a medical report template, to ensure that there are no or little waiting times when finally selecting the second set of evaluation algorithms.

According to the techniques described above, it is possible to select and trigger execution of all evaluation algorithms that fit with respect to, firstly, input data and, secondly, with respect to required output—e.g., from a perspective of the constraints imposed by the medical report template.

This can be done using the meta data. The meta data can be used to describe the kind of input/output of the respective evaluation algorithm in semantic terms using the meta data. The meta data could be indicative of one or more selected entries of a predefined set of ontologies (e.g., as commercially available under the brands SNOMED or RadLex). When identifying suitable evaluation algorithms based on the input constraints on the medical datasets and the output) using semantic terms, semantic relationships (such as "subclass of") can be exploited to identify matchings beyond identical terms. To this end, semantic reasoners can be employed. For example, given among the algorithms in there is one algorithm which can analyze the coronaries in data of type "CT angiography of coronary arteries" and one that can analyze data of type "CT of chest". Now, the medical dataset is of the type "CT angiography of coronary arteries". A match between the medical dataset and the two evaluation algorithms can be performed. The semantic reasoning may define "CT angiography of coronary arteries" as a subclass of "CT of chest"; thus, based on this knowledge both evaluation algorithms can proof suitable.

In order to determine the required output of the evaluation algorithm, report entries that are to be prefilled with outputs of the evaluation algorithm can be semantically annotated in the medical report template. Consider for example a lesion in the report of Table 2 shown above. Then, evaluations algorithm having the capability to provide the semantic description of the processable input data and the produced output data can be identified by respective meta data.

After the initial set of evaluation algorithms that should be executed has been identified, these evaluation algorithms are executed, e.g., in parallel or using multiple containers of a cloud-computing service. The outputs can be stored in a database, i.e., a structured results collection, along with the indication of the associated evaluation algorithm and the meta data.

When the user finally selects a medical report template, suitable outputs for the selected case (potentially based on multiple medical data set, e.g. multiple exams) are queried and retrieved from the database including the output.

Finally, the user can correct the output provided by the evaluation algorithm and navigate to the unstructured medical data (e.g. image study) from which the measurement was taken.

Above, the selection of one or more evaluation algorithms based on the configuration of the generation of the medical report—which configuration, in turn, can depend on the user input 112—has been explained. Turning again to FIG. 9, next, details with respect to the output of the report at box 2016 will be explained.

As illustrated in FIG. 9, the medical report 180 can be output to the user, e.g., via the HMI 214 (cf. FIG. 1). The user can then study details of the medical report 180. In particular, the medical report 180 can also include an output of the previously selected one or more evaluation algorithms. It would also be possible to output the output of the one or more evaluation algorithms. Here, a situation can occur where the user—upon studying the medical report 180 along with the output of the previously selected one or more evaluation algorithms—is not satisfied with the accuracy of the output of the one or more evaluation algorithms 711-714 or the medical report 180.

As illustrated in the scenario FIG. 9, the user can then provide a further user input 114 as feedback, e.g., via the HMI 214. The user input pertains to the medical report 180 or the output of the one or more evaluation algorithms 711-714.

To give a few examples of such user input 114 providing feedback: it would be possible that an evaluation algorithm performs a segmentation of an anatomical feature in a medical imaging dataset. For example, the evaluation algorithm could annotate a liver. Sometimes, the user may not be satisfied with the accuracy of this segmentation or annotation. Then, using the user input 114 providing feedback, the user may refine the segmentation or annotation.

Then, various scenarios are conceivable on how to use such user input 114 implementing a feedback on the medical report 180 and/or the output of the previously selected and previously executed one or more evaluation algorithms. For example, as illustrated in FIG. 9, it would be possible that the medical report 180 is re-configured, i.e., newly generated based on the feedback from the user in the form of the user input 114 (feedback loop 6001). Thus, certain changes made by the user can be included in the medical report 180 after re-executing box 2015. A further option that is illustrated in FIG. 9 (feedback loop 6002) involves re-executing at least one of the one or more evaluation algorithms by re-executing box 2014. In particular, the changes to the output of the previous execution of the one or more evaluation algorithms can be used as prior knowledge for the subsequent execution of the at least one evaluation algorithm 711-714 of the one or more evaluation algorithms 711-714 and a further iteration of box 2014. Then, based on the refined output, a re-generation of the medical report 180 can be triggered at box 2015.

There are various scenarios conceivable in which such prior knowledge is helpful when re-executing the at least one evaluation algorithm 711-714 of the one or more evaluation algorithm 711-714. For example, certain techniques of statistical learning can accommodate prior knowledge and then determine the output under consideration of this prior knowledge. For instance, are certain section of anatomical features manually segmented based on the user input 114, then this may also affect the automatic segmentation in other sections of the anatomical features. Another example pertains to the scenario illustrated in FIG. 7 with respect to the subsequently executed evaluation algorithm 711-712. For instance, the feedback implemented by the user input 114 could affect the output of the preceding evaluation algorithm 711 of the two inter-dependent evaluation algorithm 711-712. Then, re-execution can be triggered for the subsequent algorithm 712.

Figure 11:
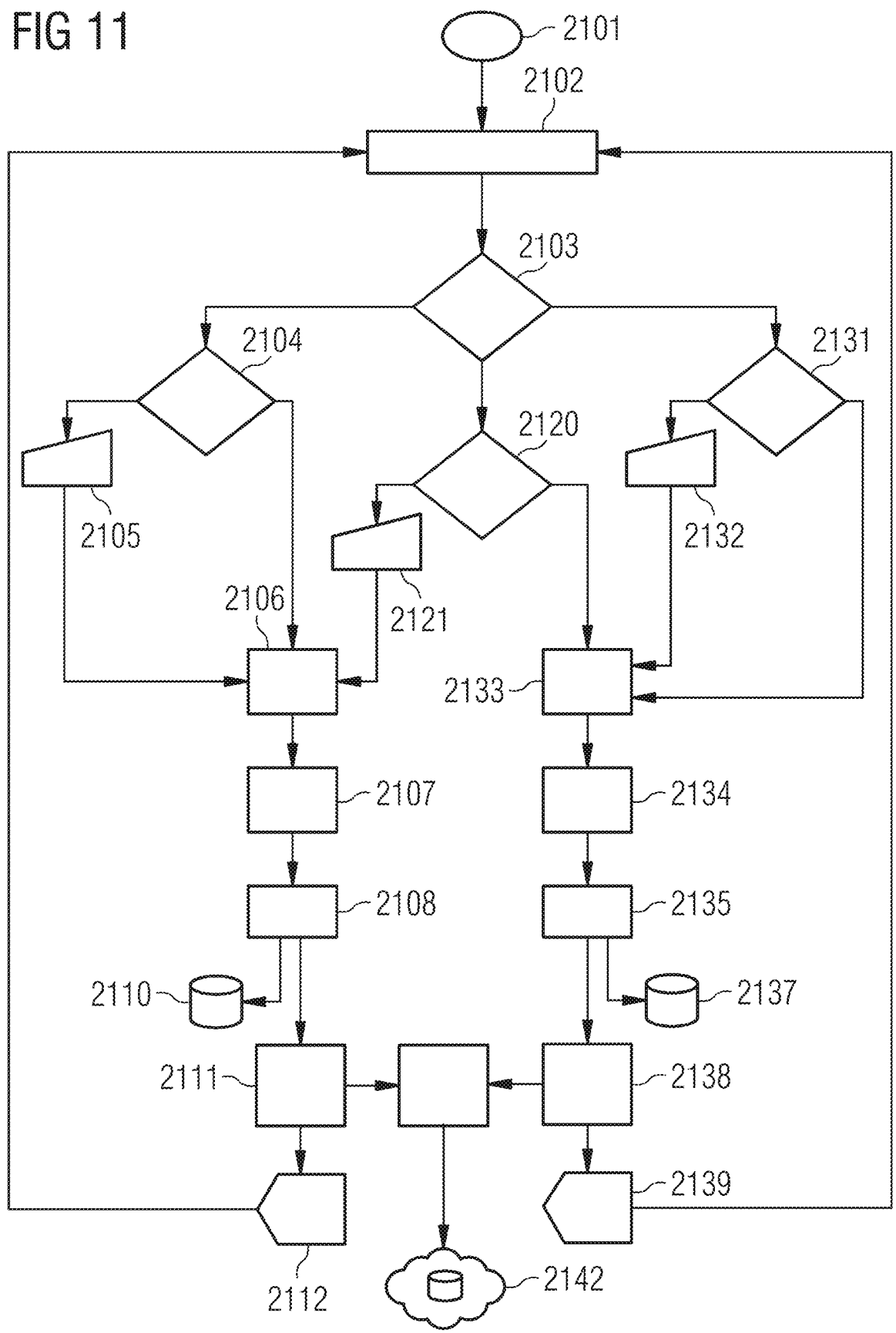
FIG. 11 is a flowchart of a method according to various examples.

FIG. 11 is a flowchart of a method according to various examples. FIG. 11 illustrates an example of an overall process associated with the clinical workflow for evaluation of one or more medical data sets and the generation of a medical report. FIG. 11, in particular, illustrates aspects with respect to various options for implementing computer-implemented logic using on-premise and off-premise computational resources.

FIG. 11 depicts a high-level concept diagram of the medical analytics platform. FIG. 11 generally relates to a scenario in which one or more medical data sets are received from one or more of the following: an imaging modality; a laboratory; a hospital information system; etc. For example, a medical data Gateway can act as a repository for such medical data sets. Then, the evaluation of the one or more medical data sets can be performed off-premise, e.g., using a cloud-computing service, or on-premise (cf. FIG. 1: central server 221 and local server 213).

In both scenarios—i.e., off-premise evaluation, as well as on-premise evaluation—the selection of the one or more evaluation algorithms can be automatic, semi-automatic, or manually. Also, the execution of the selected one or more evaluation algorithms can be triggered automatically, semi-automatically, or manually.

Figure 12:
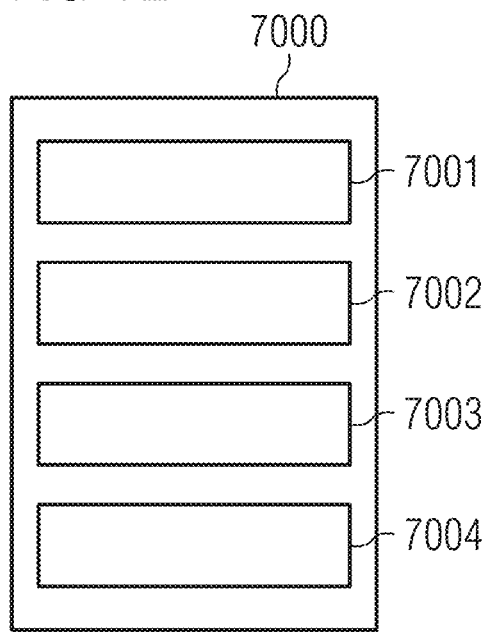
FIG. 12 schematically illustrates an algorithm runtime infrastructure according to various examples.

The method of FIG. 11 can be implemented by software modules. Such software modules 7001-7004 are illustrated in FIG. 12. Hereinafter, reference is made to a combination of FIG. 11 and FIG. 12.

For instance, consider an on-premise automatic trigger. Here, it would be possible that a medical data gateway notifies an algorithm runtime infrastructure 7000 that implements an algorithm selection module 7001, e.g., implemented in software on the server 213 (cf. FIG. 1). For example, the algorithm selection module 7001—even in an on-premise scenario—could be implemented using a computational resource management relying on containers, as explained above with respect to the cloud-computing service 601 (cf. FIG. 5). Then, an algorithm execution module 7002 can execute one or more selected evaluation algorithms. Then, a medical reporting module 7003 can generate the medical report. The operation of all modules 7001-7003 can be subject to user interaction via a user-interface module 7004.

A cloud-based implementation can follow a similar strategy as outlined above in connection with the on-premise automatic/manual trigger. Here, the one or more of the modules 7001-7004 can be implemented by a cloud-computing service.

Now, details with respect to the process flow of FIG. 11 are explained. This process flow can be implemented using the algorithm runtime infrastructure 7000.

The process starts at box 2101. At box 2102, one or more medical data sets of the patient are obtained. This can include a data collection via a medical data gateway. A query can be performed, e.g., from a Hospital Information System (HIS) or a Radiology Information System (RIS), and/or Picture Archiving and Communication System (PACS).

At box 2103, next, a deployment scenario is selected. This can involve the selection of the appropriate distribution of computational tasks between on-premise and off-premise execution, e.g., involving cloud-computing services.

Depending on the check at box 2103, the following options are available: box 2104 is executed for an on-premise scenario; box 2131 is executed for an off-premise scenario; and box 2120 is executed for a hybrid scenario.

At each one of boxes 2104, 2120, and 2131, a respective selection between one or more user-interaction modes is made. In particular, a selection between an automatic user-interaction mode or a manual user-interaction mode is made, for the selection of one or more evaluation algorithms.

In case a (semi-)manual user-interaction mode is selected, then, at boxes 2105, 2121, or 2132, user input is received and, thereby, the user can select one or more evaluation algorithms for execution. For instance, this may include a selection from a ranked list (cf. TAB. 1). Optionally, the user may also select the medical report template, thereby performing a configuration of the generation of the medical report. Otherwise, the selection is automatically implemented.

In any case, at box 2106 or at box 2133 the selection of the one or more evaluation algorithms is triggered. At box 2106, the on-premise algorithm selection module 7001 can be used; while at box 2133, the off-premise algorithm selection module 7002 is used.

Next, at box 2107 or at box 2134, execution of the selected one or more evaluation algorithms is triggered and performed. This includes interfacing to an on-premise or off-premise execution module 7002, respectively.

At optional boxes 2108 and 2135, compute containers can instantiated and executed for each selected evaluation algorithm. At box 2108 the compute containers are defined in connection with the on-premise algorithm runtime infrastructure of box 2107. At box 2135 compute containers are instantiated and executed for each selected evaluation algorithm of box 2133, wherein the compute containers are defined in connection with the cloud-computing service.

The output of the one or more evaluation algorithms can then be stored, at box 2110 or at box 2137, respectively; e.g., in a RIS, HIS, or PACS.

The output of the one or more evaluation algorithms can also be output to the user, at box 2111 or at box 2138, respectively. This may be implemented by using the user-interfacing module 7004. The user-interfacing module 7004 can access the HMI 214.

At box 2111 or box 2138, it would also be possible that a medical report is generated. This can be done using the reporting module 7003. The medical report can be pre-filled based on an output of the evaluation algorithms, in accordance with a medical report template.

At box 2111 or at box 2138, it would optionally be possible to configure the generation of the medical report, e.g., based on the medical report template (e.g., if the configuration has not already been performed at box 2105 or 2132 or 2121). The appropriate medical report template could be selected automatically or semi-automatically or manually. Such and other tasks related to the output and the generation of a medical report can be implemented using on-premise compute resources, for box 2111, or using off-premise compute resources such as a cloud-computing service.

Then, at box 2141, the medical report could be uploaded to a repository, e.g., a HIS, RIS, or PACS. The storage is illustrated in box 2142.

In some examples, at box 2112, or at box 2139 respectively, the user is presented with the output of the one or more evaluation algorithms and/or with the medical report that has been generated in box 2111 or box 2138, respectively. The user then has a chance to refine or modify the output of the one or more evaluation algorithms and/or the medical report; then, based on such user feedback box 2102 and following are re-executed (cf. FIG. 9: user feedback 114). For example, quantitative results of the evaluation algorithms could be edited. For example, a segmentation could be edited.

Summarizing, above techniques have been described that facilitate an efficient and lean workflow for the automated evaluation of one or more medical data sets, and the automatic generation of medical reports based on outputs of respective evaluation algorithms. In particular, the various evaluation algorithms can be semantically labeled using meta data which can facilitate the selection of the appropriate evaluation algorithms. A generic repository of evaluation algorithms can be kept, together with the metadata.

According to some examples, a report-driven clinical workflow is implemented. Here, the selection of the evaluation algorithms used for the medical reporting depends on the selection of the medical report template used for configuring the generation of the medical report itself.

The proposed techniques enable generic and scalable storage of evaluation algorithms. The algorithm repository can easily be extended by arbitrary algorithms. Thereby, there is the capability to handle different unstructured types of medical dataset and various medical report types. These can easily be provided by third parties.

The collection of employed evaluation algorithms as well as reporting templates can easily be customized to individual users and customers of the solution, thus respecting personal preferences for certain providers.

By not exposing all the results of all executed evaluation algorithms on the medical datasets, but only exposing the results of a subset of selected evaluation algorithms—e.g., the selection depending on the selected report template—, it is avoided to show distracting results to the user which could lead to false positives (less diagnostic accuracy) as well as slow down the workflow.

Although the invention has been shown and described with respect to certain preferred embodiments, equivalents and modifications will occur to others skilled in the art upon the reading and understanding of the specification. The present invention includes all such equivalents and modifications and is limited only by the scope of the appended claims.

For illustration, various examples have been described which rely on a certain distribution of computational resources, e.g., between a server in a local area network and a central server. In other examples, the same functionality may be implemented using a different distribution of computational resources. In this regard, some techniques have been described in connection with a certain structure of databases. In general, it would be possible to integrate certain information content described in connection with two separate databases into a single database. Also, meta data and algorithms may be stored in separate databases (cf. FIG. 2-3).

For further illustration, various examples have been described in connection with a server that implements certain logic, e.g., by using a control circuitry that is configured to load and execute program code. In the various examples described herein, it is possible that other kinds and devices—beyond a server—include a control circuitry that is configured to load and execute such program code. Other devices include, e.g., a medical imaging apparatus, a personal computer, a laptop, a tablet, etc. The program code could be provided by a computer program or a computer program product or a computer-readable storage medium.

For still further illustration, it would be possible that the various techniques described herein in connection with a method are rather implemented by a device or a computer program or a computer program product or a computer-readable storage medium.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method, comprising:
    obtaining one or more medical datasets of a patient;
        performing a configuration of a generation of a medical report including a selection of a report template of the medical report from a report repository;
    selecting, using a selection algorithm, one or more algorithms from an algorithm repository including multiple candidate algorithms based on the one or more medical datasets, a user input, and the configuration of the generation of the medical report, the selecting including:
        providing the one or more medical datasets as an input to one or more further algorithms, triggering execution of the one or more further algorithms, at least one of the one or more further algorithms being configured to perform a landmark detection of physiological features in the one or more medical datasets, and selecting the one or more algorithms based on meta data associated with the multiple candidate algorithms and the physiological features obtained from the landmark detection by comparing the meta data and the physiological features, the comparing including a semantic reasoning based on a knowledge graph associated with one or more of:
  physiological features;
  body regions;
  diseases:
  imaging modalities; or
  types of medical datasets,
providing the one or more medical datasets as an input to the one or more algorithms;
executing the one or more algorithms using a respective dedicated container of a cloud-computing service, the one or more algorithms configured to evaluate the one or more medical datasets and the respective dedicated container of each of the one or more algorithms being instantiated upon execution of each of the one or more algorithms;
generating the medical report based on an output of at least one of the one or more algorithms;
transmitting the output of the one or more algorithms to a human-machine interface as a first user output;
receiving feedback associated with the output of the one or more algorithms from the human-machine interface;
triggering, based on the feedback, a re-execution of at least one of the one or more algorithms using the respective dedicated container of the cloud-computing service, the feedback being an input into the at least one of the at one or more algorithms;
generating an updated medical report based on an updated output of the at least one of the one or more algorithms;
transmitting the updated medical report to the human-machine interface as a second user output; and training the selection algorithm using recurrent training based on the user input.

2. The method of claim 1,
wherein the one or more algorithms are selected during the triggering based on an output of the one or more further algorithms.

3. The method of claim 2,
wherein the one or more medical datasets include a medical imaging dataset.

4. The method of claim 3,
wherein the meta data is indicative of a physiological-diagnostic content description of at least one of the input and the output of the multiple candidate algorithms.

5. The method of claim 1, further comprising:
providing access to the algorithm repository to enable third parties to upload new candidate algorithms along with corresponding meta-data.

6. The method of claim 1,
wherein the one or more further algorithms are trained based on the user input.

7. The method of claim 1,
wherein the execution of the one or more further algorithms is implemented using a pre-instantiated container of the cloud-computing service.

8. The method of claim 1, further comprising:
selecting between multiple user-interaction modes for the selection of the one or more algorithms,
wherein the selecting of the one or more algorithms is further based on the user input received from the human-machine interface in accordance with a selected user-interaction mode of the multiple user-interaction modes.

9. The method of claim 8,
wherein the multiple user-interaction modes vary with respect to a degree of automation of the selecting of the one or more algorithms.

10. The method of claim 8,
wherein the selecting between the multiple user-interaction modes is based on an accuracy feedback of previous selections of the one or more algorithms.

11. The method of claim 10,
wherein the accuracy feedback is determined based on a count of re-selections of the one or more algorithms based on user inputs received from the human-machine interface.

12. The method of claim 1,
wherein the selecting of the one or more algorithms comprises a pre-selection of a first set of algorithms from the algorithm repository based on the one or more medical datasets,
wherein the selecting of the one or more algorithms includes a post-selection of a second set of algorithms based on the configuration of the generation of the medical report, the second set of algorithms being a subset of the first set of algorithms.

13. The method of claim 1, further comprising:
transmitting the medical report to the human-machine interface;
receiving user feedback associated with the medical report from the human-machine interface; and
triggering, based on the user feedback received, a re-generation of the medical report.

14. The method of claim 1,
wherein the feedback is associated with an output of a first algorithm of the one or more algorithms,
wherein re-execution of a second algorithm of the one or more algorithms is triggered based on the feedback associated with the output of the first algorithm, the input of the second algorithm being dependent on an output of the first algorithm.

15. The method of claim 1, further comprising:
obtaining a patient dataset including patient-specific information of the patient,
wherein the selecting of the one or more algorithms is further based on the patient dataset.

16. The method of claim 10, wherein the accuracy feedback specifies whether the output of the one or more algorithms is satisfactory for a clinical task and a re-selection indicates that the output of the one or more algorithms is not satisfactory.

* * * * *